(12) United States Patent
Lee et al.

(10) Patent No.: US 11,813,461 B2
(45) Date of Patent: *Nov. 14, 2023

(54) DEVICE AND METHOD MODULATING NERVE OF A PATIENT BY PROVIDING ELECTRICAL STIMULATION

(71) Applicant: Y-BRAIN INC., Seongnam-si (KR)

(72) Inventors: Ki Won Lee, Seongnam-si (KR); Hyeri Sim, Seongnam-si (KR); Yuhee Kim, Seongnam-si (KR)

(73) Assignee: Y-BRAIN INC., Seongnam-si (KR)

( * ) Notice: Subject to any disclaimer, the term of this patent is extended or adjusted under 35 U.S.C. 154(b) by 114 days.

This patent is subject to a terminal disclaimer.

(21) Appl. No.: 17/468,521

(22) Filed: Sep. 7, 2021

(65) Prior Publication Data
US 2021/0402188 A1 Dec. 30, 2021

Related U.S. Application Data

(63) Continuation of application No. 16/705,563, filed on Dec. 6, 2019, now Pat. No. 11,141,593.

(51) Int. Cl.
*A61N 1/36* (2006.01)

(52) U.S. Cl.
CPC ......... *A61N 1/36178* (2013.01); *A61N 1/361* (2013.01); *A61N 1/36034* (2017.08); *A61N 1/36053* (2013.01); *A61N 1/36064* (2013.01); *A61N 1/36075* (2013.01); *A61N 1/36085* (2013.01); *A61N 1/36096* (2013.01)

(58) Field of Classification Search
CPC .................................................. A61N 1/36034
See application file for complete search history.

(56) References Cited

U.S. PATENT DOCUMENTS

| | | | | |
|---|---|---|---|---|
| 4,924,880 A | * | 5/1990 | O'Neill | A61N 1/36021 607/66 |
| 5,117,826 A | * | 6/1992 | Bartelt | A61N 1/36021 607/46 |
| 8,060,208 B2 | * | 11/2011 | Kilgore | A61N 1/36071 607/46 |
| 8,731,657 B1 | * | 5/2014 | Shambayati | A61N 1/36031 606/42 |
| 11,141,593 B2 | * | 10/2021 | Lee | A61N 1/36075 |
| 2004/0044338 A1 | * | 3/2004 | Lennox | A61N 1/326 606/32 |
| 2005/0149148 A1 | * | 7/2005 | King | A61N 1/39624 607/46 |
| 2015/0032180 A1 | * | 1/2015 | Bollen | A61N 1/3752 607/46 |
| 2016/0008620 A1 | * | 1/2016 | Stubbeman | A61B 5/4848 607/45 |

* cited by examiner

*Primary Examiner* — Eric D. Bertram
(74) *Attorney, Agent, or Firm* — Studebaker & Brackett PC (57) ABSTRACT

Disclosed is a device for modulating a nerve of a patient by applying electrical stimulation to the nerve of the patient. The device includes a stimulation module that applies a signal to the nerve of the patient, and a controller that controls a signal to be applied to the stimulation module, wherein the signal to be applied to the stimulation module includes pulse bursts and a direct current (DC) waveform.

13 Claims, 7 Drawing Sheets

| | Pulse (mA) | Pulse Frequency (Hz) | Pulse duration (µs) | inter pulse duration (µs) | ramp up (s) | ramp down (s) | Total Time (s) | Burst Frequency | Burst Duration (ms) | DC (mA) | Target |
|---|---|---|---|---|---|---|---|---|---|---|---|
| 1 | 20 | 10000 | 45 us | 5 us | 150 | 150 | 600 | 10 | 20ms | 0.5 (-/+) | VNS |
| 2 | 10 | 2000 | 100 us | 5 us | 150 | 150 | 600 | 5 | 70ms | 0.5 (+/-) | CNS |
| 3 | 10 | 10000 | 45 us | 5 us | 150 | 150 | 600 | 10 | 30ms | 0.5 | TNS |

DEVICE AND METHOD MODULATING NERVE OF A PATIENT BY PROVIDING ELECTRICAL STIMULATION

CROSS-REFERENCE TO RELATED APPLICATIONS

This application is a Continuation of U.S. Pat. No. 11,141,593, issued on Oct. 12, 2021, which was U.S. patent application Ser. No. 16/705,563, filed Dec. 6, 2019, the entire content of which is incorporated herein by reference.

BACKGROUND

Embodiments of the inventive concept described herein relate to a device for modulating a nerve by applying electrical stimulation to the nerve of a patient, and a method for treating a medical condition of the patient using such a device. More specifically, a signal applied to the neve for electrical stimulation includes pulse bursts and a direct current waveform.

Various attempts have been made to treat medical conditions of patients by applying electrical stimulation to nerves thereof.

First, in an implant type scheme, modulation of a nerve of a patient is executed by inserting a device into a body in an invasive manner and applying electrical stimulation directly to the nerve. A representative example of the implant type scheme include electrical stimulation to alleviate a major symptom of asthma or COPD. In this way, while reducing a side effect caused by a conventional nerve cutting scheme, the main symptom of asthma or COPD may be alleviated.

Second, in a non-implant type scheme, electrical stimulation is applied to an epidermis non-invasively to reach the nerve. A representative example of the non-implant type scheme includes alleviating an ADHD symptom by applying electrical stimulation. In this way, this scheme may obtain an effect of reducing a side effect caused by the invasive treatment and thus may replace a conventional invasive treatment.

SUMMARY

Embodiments of the inventive concept provide a nerve modulation device and method that may modulate a nerve of a patient by applying a signal including pulse bursts and a direct current waveform thereto and thus applying electrical stimulation to the nerve.

Embodiments of the inventive concept provide a nerve modulation device and method that may treat a medical disorder of a patient by applying a signal including pulse bursts and a direct current waveform thereto in a non-invasive manner and thus applying electrical stimulation to the nerve of the patient.

The purposes to be achieved by the inventive concept are not limited to the purposes mentioned above. Still other purposes as not mentioned will be clearly understood by those skilled in the art from following descriptions.

According to an exemplary embodiment, a device for modulating a nerve of a patient by applying electrical stimulation to the nerve of the patient includes a stimulation module to apply a signal to the nerve of the patient; and a controller to control a signal to be applied to the stimulation module, wherein the signal to be applied to the stimulation module includes pulse bursts and a direct current (DC) waveform.

According to an exemplary embodiment, a method for treating a medical condition of a patient includes positioning a stimulation module onto a target region of an outer surface of the patient; generating a signal including pulse bursts and a direct current (DC) waveform; and applying the signal to the stimulation module such that electrical stimulation is non-invasively applied to the nerve through the outer surface.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Advantages and features of the inventive concept, and methods of achieving them will become apparent with reference to embodiments described below in detail in conjunction with the accompanying drawings. However, the inventive concept is not limited to the embodiments disclosed below, but may be implemented in various forms. The present embodiments are provided to merely complete the disclosure of the inventive concept, and to merely fully inform those skilled in the art of the inventive concept of the scope of the inventive concept. The inventive concept is only defined by the scope of the claims.

The terminology used herein is for the purpose of describing the embodiments only and is not intended to limit the inventive concept. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. The same reference numbers in different figures denote the same or similar elements, and as such perform similar functionality. As used herein, the term "and/or" includes any and all combinations of one or more of the associated listed items. Although "first", "second", etc. are used to describe various components, these components are not limited by these terms. These terms are only used to distinguish one component from another. Therefore, a first component mentioned below may be a second component within a technical spirit of the inventive concept.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
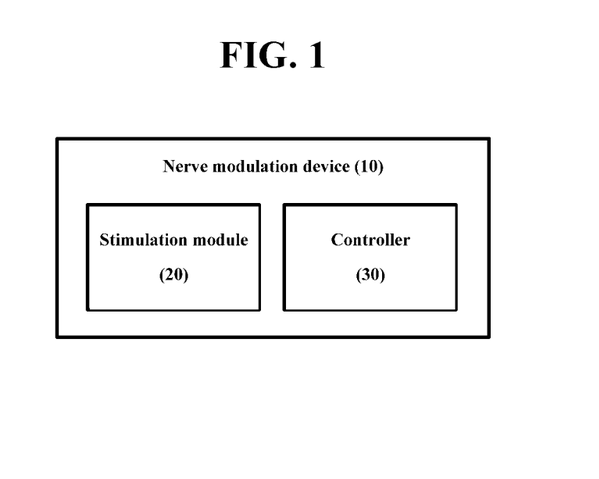
FIG. 1 is a diagram of a nerve modulation device according to an embodiment of the inventive concept.
Figure 2:
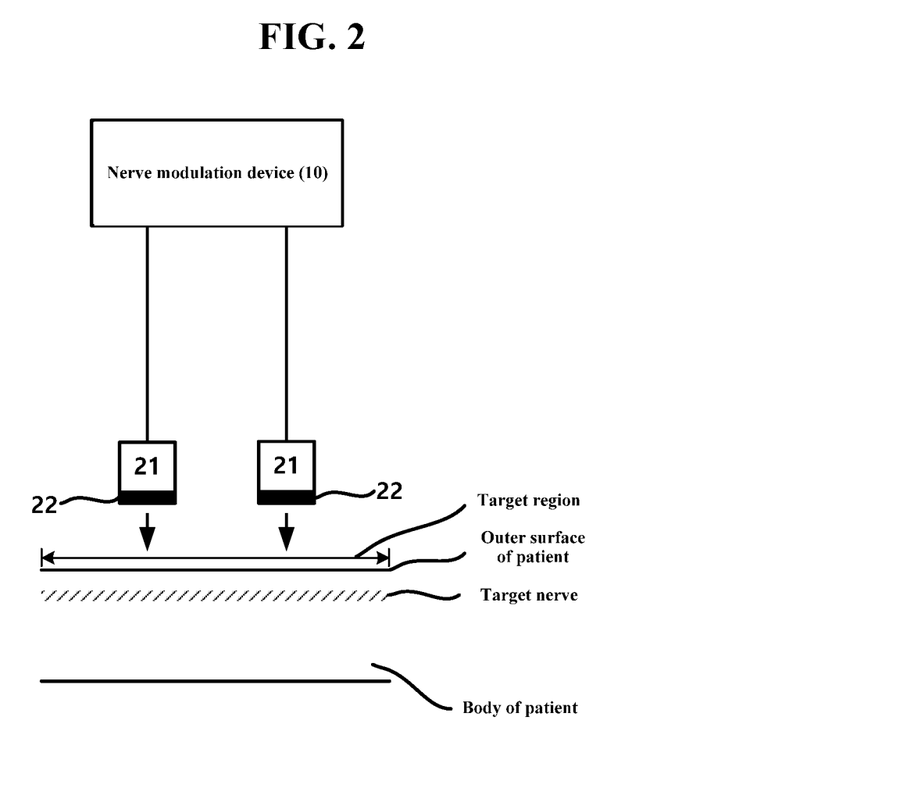
FIG. 2 is a diagram showing a detailed configuration of a stimulation module included in FIG. 1.
Figure 3:
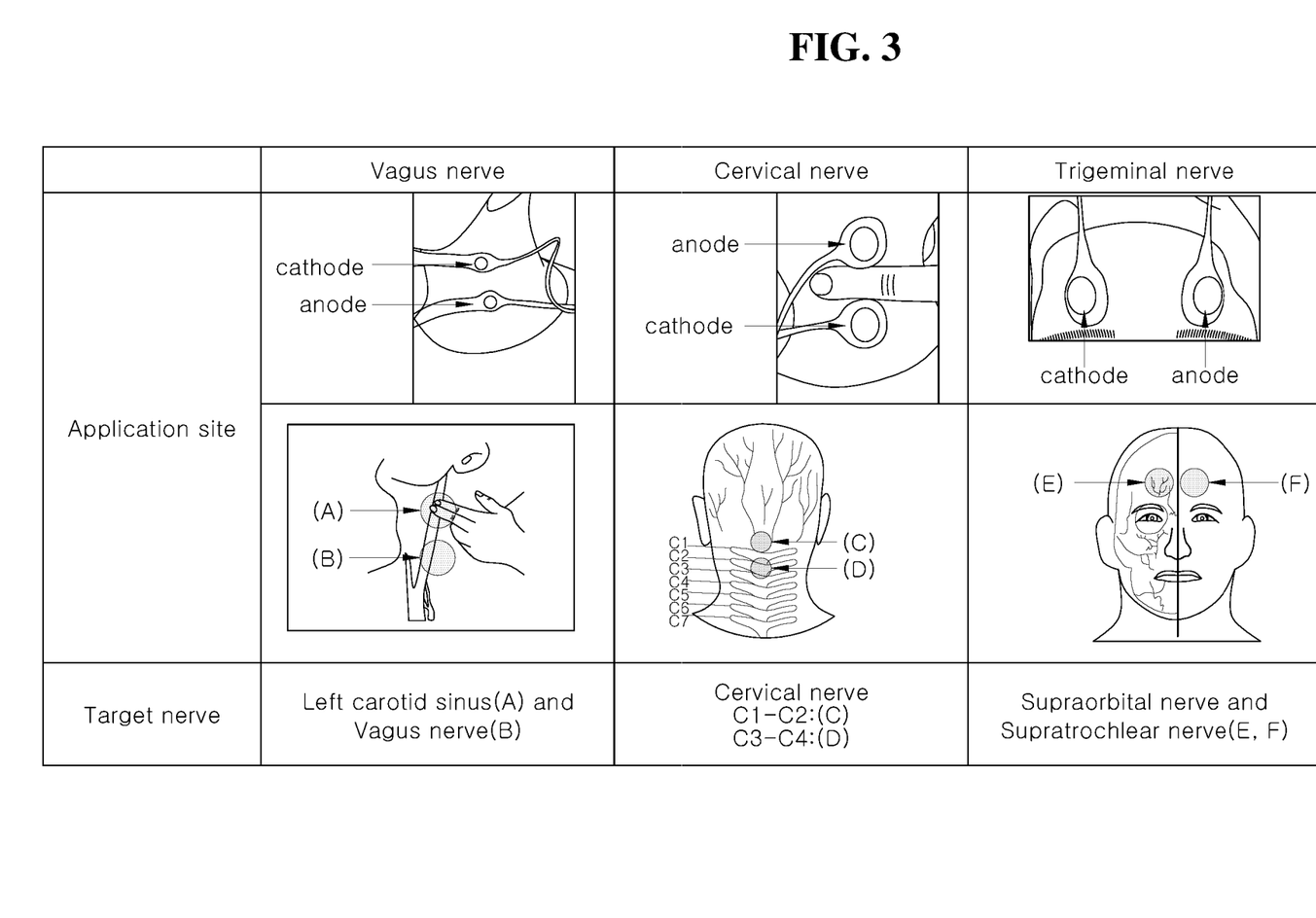
FIG. 3 is a view for explaining a stimulation target site according to a target nerve.
Figure 4:
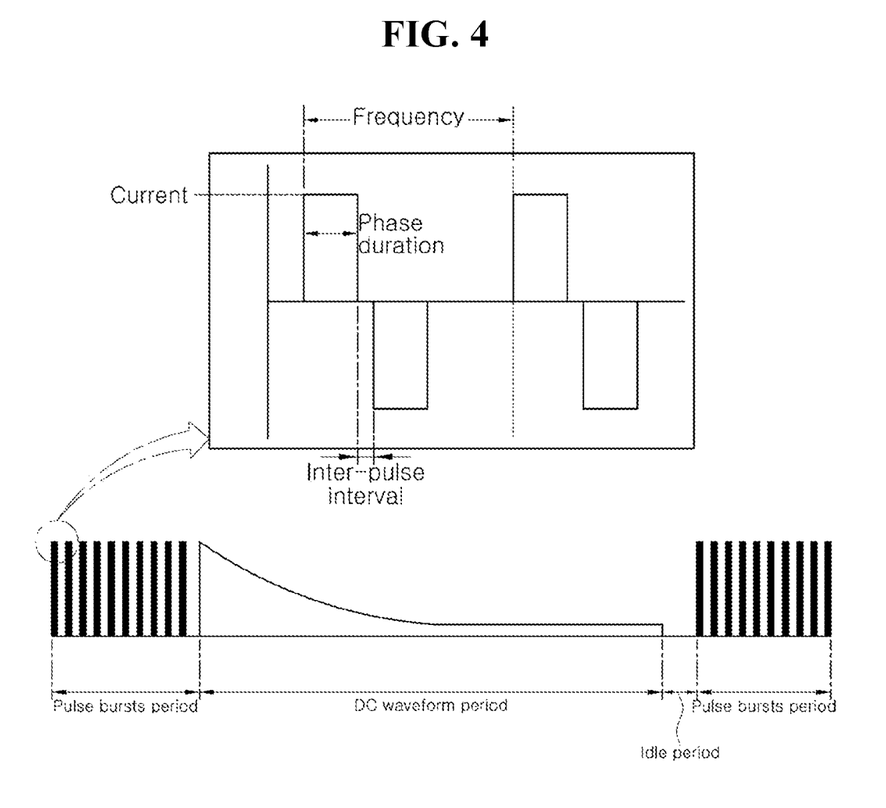
FIG. 4 illustrates a signal for electrical stimulation by the nerve modulation device.
Figure 5:
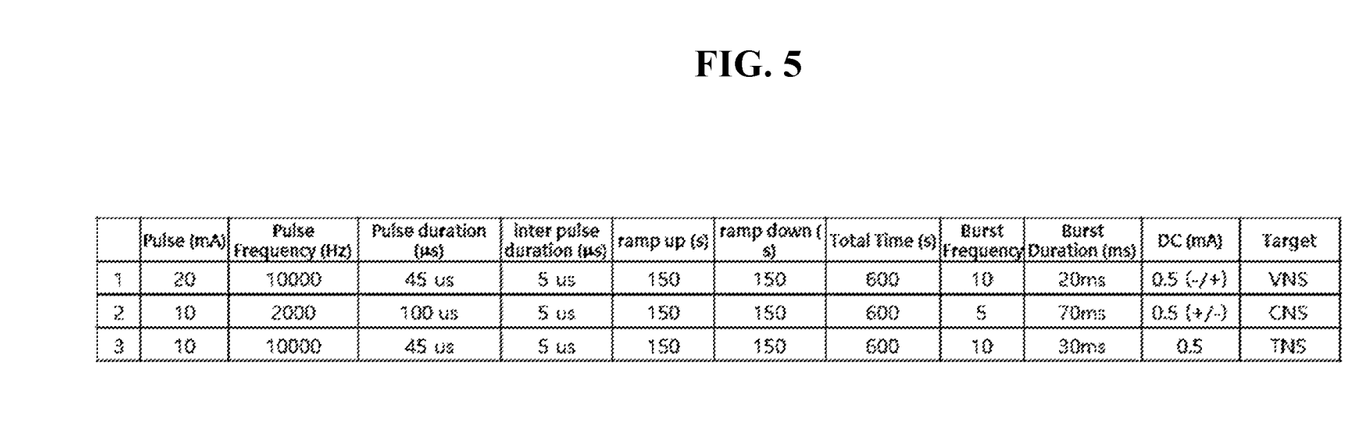
FIG. 5 is a table related to a configuration of a pulse bursts characteristic and a direct current waveform characteristic in the nerve modulation device.
Figure 6A:
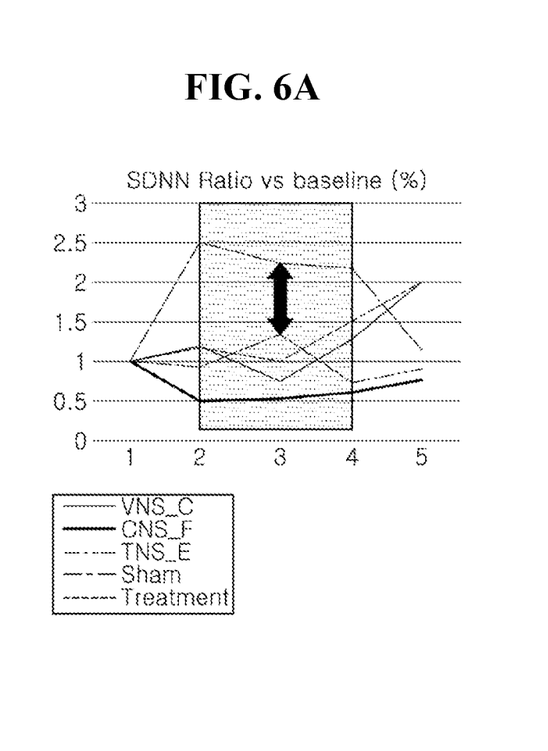
FIGS. 6A and 6B are graphs that may identify an effect of using the nerve modulation device as a HRV major indicator.
Figure 6B:
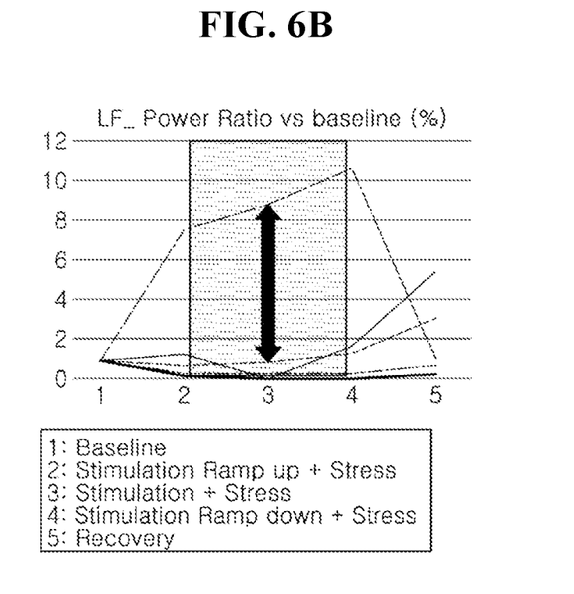
Figure 7A:
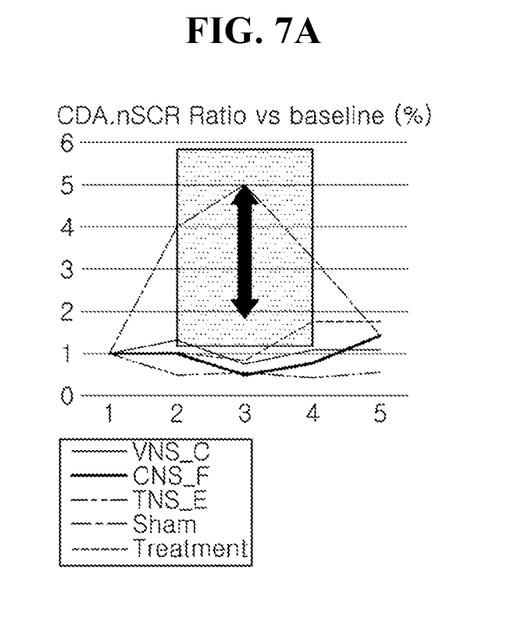
FIGS. 7A and 7B are graphs that may identify an effect of using the nerve modulation device as an EDA major indicator.
Figure 7B:
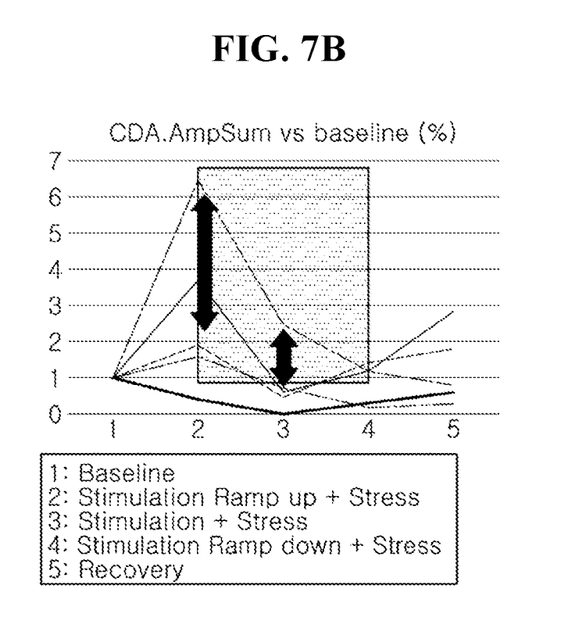

Hereinafter, a nerve modulation device 10 according to an embodiment of the inventive concept will be described with reference to FIGS. 1 to 7. FIG. 1 is a diagram of the nerve modulation device 10 according to an embodiment of the inventive concept. FIG. 2 is a diagram showing a detailed configuration of a stimulation module 20 included in FIG. 1. FIG. 3 is a view for explaining a stimulation target site according to a target nerve. FIG. 4 illustrates a signal for electrical stimulation by the nerve modulation device 10. FIG. 5 is a table related to a configuration of a pulse bursts characteristic and a direct current waveform characteristic in the nerve modulation device 10. FIG. 6 is a graph that may identify an effect of using the nerve modulation device 10 as a HRV major indicator. FIG. 7 is a graph that may identify an effect of using the nerve modulation device 10 as an EDA major indicator.

The nerve modulation device 10 according to the present embodiment is a device for applying electrical stimulation to the patient's nerve and thus modulating the nerve. The nerve modulation device 10 is configured to apply electrical stimulation to the patient's nerve and thus modulate the nerve to treat the patient's medical condition.

In this connection, modulating the nerve means to modulate nerve activity. The nerve activity may mean, for example, an amplitude, frequency and/or pattern of an action potential in the nerve. In some embodiments, modulating the nerve may include modulating nerve activity of a sympathetic or parasympathetic nerve system.

Modulation of the nerve (or modulation of the nerve activity) means that the nerve activity is changed as the electrical stimulation is applied to the nerve. In some embodiments, the nerve activity may be increased, suppressed (or blocked) according to nerve modulation, and, the amplitude and/or frequency of the action potential in the nerve may be altered, after the electrical stimulation is applied, compared to the nerve activity before the electrical stimulation is applied. In some embodiments, the pattern of the action potential may be changed according to the modulation of the nerve before or after the electrical stimulation is applied.

The nerve modulation device 10 may provide an effective treatment of a medical condition of the patient in that the medical condition of the patient may be alleviated or suppressed according to the modulation of the nerve.

Referring to FIG. 1, the nerve modulation device 10 according to an embodiment of the inventive concept includes the stimulation module 20 and a controller 30. In some embodiments, the nerve modulation device 10 may include a larger or smaller number of components than the number of the components shown in FIG. 1.

In some embodiments, the components of the nerve modulation device 10 may be physically spaced apart from each other and may not necessarily be located in a single housing.

In some embodiments, the nerve modulation device 10 may be a standing type device positioned next to the patient, a portable type device that the patient or medical staff may carry and move, or a wearable type device that the patient may wear, but is not limited thereto.

The stimulation module 20 is configured to apply a signal to the nerve of the patient. An operation thereof is controlled by the controller 30 to be described later. The stimulation module 20 may include at least one component necessary to apply a signal to the nerve of the patient. For example, the stimulation module 20 may include, but is not limited to, a power source (not shown), an electrode 21 and a contact surface 22 located on a target region of the patient's outer surface. The electrode 21 may include an anode and a cathode as a plurality of electrodes 21.

In this connection, when the contact surface 22 of the stimulation module 20 is located on the target region of the outer surface of the patient, a signal for the electrical stimulation may be applied to the nerve non-invasively through the outer surface. Specifically, because an electric field generated when the signal for electrical stimulation is applied passes through the outer surface of the patient and is transmitted to the nerve inwardly of the outer surface of the patient, the electrical stimulation may be applied to the nerve in a non-invasive manner using the nerve modulation device 10 according to an embodiment of the inventive concept.

However, in some embodiments, the nerve modulation device 10 of the inventive concept may apply the electrical stimulation to the nerve of the patient not non-invasively but invasively. For example, the nerve modulation device 10 may be mounted in the patient's body in an implant type scheme.

Referring to FIG. 2, the target region of the patient's outer surface may be an outer surface on a region where the target nerve to be subjected to the electrical stimulation is located. The target nerve may be a nerve that requires the application of the electrical stimulation thereto to treat the medical condition of the patient. For example, the anode and the cathode as the plurality of electrodes 21 may be spaced apart from each other and may be disposed on the outer surface of the region where the target nerve is located. The target nerve may be located below a outer surface where the anode and cathode are located.

The target region may be at least one of forehead, ear, neck and wrist. The target nerve may include at least one of a cranial nerve, a carotid sinus nerve, a vagus nerve, a cervical nerve, and a median nerve. The medical condition of the patient to be treated may be at least one of migraine, insomnia, neurologic disorder, neuropathic pain, motor dysfunction, epilepsy, tinnitus, obesity and depression. However, the present disclosure is not limited thereto.

Referring to FIG. 3, when each of a left carotid sinus nerve "A" and a left vagus nerve "B" is the target nerve, a stimulation target site as a target region may be an outer surface of a side of the patient's neck where the left carotid sinus nerve "A" and the left vagus nerve "B" are located. Specifically, the cathode may be located on the outer surface on the left carotid sinus nerve "A", while the anode may be located on the outer surface on the left vagus nerve "B". The cathode may be located closer to a head than the anode may be.

When the neck nerve is the target nerve, a stimulation target site as a target region may be an outer surface of a back of the patient neck where the neck nerve is located. Specifically, the stimulation target site may be an outer surface "C" adjacent to a first cervical vertebral C1 and a second cervical vertebral C2, and an outer surface "D"

adjacent to a third cervical vertebral C3 and a fourth cervical vertebral C4. The anode may be located on the outer surface "C" adjacent to the first cervical vertebral C1 and the second cervical vertebral C2, while the cathode may be located on the outer surface "D" adjacent to the third cervical vertebral C3 and the fourth cervical vertebral C4. The anode may be located closer to the head than the cathode may be.

In addition, when a trigeminal nerve belonging to the cranial nerve is the target nerve, a stimulation target site as a target region may be an outer surface "E" of a right eyebrow and an outer surface "F" of a left eyebrow where a supraorbital nerve and a supratrochlear nerve are located which are a first branch of an opthalmic nerve as a branch of the trigeminal nerve. Specifically, the cathode may be located on the outer surface "E" of a right supraorbital nerve and a right supratrochlear nerve, while the anode may be located on the outer surface "F" of a left supraorbital nerve and a left supratrochlear nerve.

The controller 30 controls the nerve modulation device 10, specifically, the signal to be applied to the stimulation module 20. In this connection, the signal is an electrical signal for electrical stimulation, and includes pulse bursts and a direct current (DC) waveform.

Referring to FIG. 4, the electrical stimulation means an electrical signal. The electrical signal include pulse bursts and a direct current (DC) waveform. The signal is divided, in a time series manner, into a pulse bursts period and a direct current waveform period. The controller 30 controls the signal so that the direct current waveform period is located, in a time series manner, between adjacent pulse bursts periods. In more detail, the pulse bursts period and the direct current waveform period may be arranged alternately.

In some embodiments, the pulse bursts period and the direct current waveform period do not overlap each other. The controller 30 may control the signal such that the pulse bursts are contained in the pulse bursts period and no direct current waveform is contained in the pulse bursts period, and, subsequently, an application of the pulse bursts is stopped in the direct current waveform period but the direct current waveform is contained in the direct current waveform period. Because the pulse bursts and the direct current waveform are generated from the same power source (not shown), the pulse bursts period and the direct current waveform period may not overlap each other.

Referring to a region where the pulse bursts period is transitioned to the direct current waveform period, each pulse has a first current value in the pulse bursts period, and the direct current waveform has a second current value different from the first current value in the direct current waveform period. That is, the first current value may be a target current value of the pulse and the second current value may be a target current value of the direct current waveform. Because the nerve modulation device 10 according to the present embodiment generates the signals having current values varying in a time series manner in the same stimulation module 20, it is difficult to change the first current value to the second current value in a discrete manner due to circuit characteristics.

Therefore, in the direct current waveform period, the signal includes a waveform in which a current value is continuously changed from the first current value to the second current value. When the first current value is relatively larger than the second current value, in the direct current waveform period, a direct current waveform includes a waveform in which a current value decreases from a relatively large first current value to a relatively small second current value.

In the direct current waveform period, the direct current waveform may be configured such that a current value reaches the second current value and then maintains substantially the second current value for a predetermined time. Because, in the direct current waveform period, electrical stimulation to the nerve of the patient is to be executed using the direct current waveform having the second current value, a situation as described above in which a current value of the direct current waveform reaches the second current value and then is maintained to be the second current value for a predetermined time.

In this connection, a descent slope value of the direct current waveform in the direct current waveform period may be determined based on the medical condition of the patient to be treated. For example, based on the medical condition of the patient, the first current value of each pulse included in the pulse bursts period, the second current value of the direct current waveform in the direct current waveform period, and other characteristics may be determined. Thus, the descent slope value of the direct current waveform in the direct current waveform period may be determined based on the medical condition of the patient.

Therefore, when the medical condition of the patient changes, at least one of a characteristic of the pulse bursts and a characteristic of the direct current waveform for treatment may change. Accordingly, not only the descent slope value of the direct current waveform in the direct current waveform period may change, but also, a length of an idle period between the direct current waveform period and the pulse bursts period may change. The characteristic of the pulse bursts and the characteristic of the direct current waveform may include a first current value (mA), a frequency (Hz), a pulse duration (μs), an inter-pulse duration (82 s), a ramp up (s), ramp down (s), a total time (s), a burst frequency (Hz), and a burst duration (ms) of a pulse included in the pulse bursts period, and a second current value (mA) of the direct current waveform.

In some embodiments, referring to FIG. 4 and a region in which the direct current waveform period is switched to the pulse bursts period, the direct current waveform has a second current value in the direct current waveform period, and each pulse in the pulse bursts period has a first current value that is different from the second current value. Therefore, a region in which the direct current waveform period is transitioned to the pulse bursts period includes an idle period. The idle period refers to a period during which the simulation module 20 does not output a current temporarily. During the idle period, no direct current waveform or pulse bursts are output. Specifically, when the pulse bursts period is subsequent to the direct current waveform period in a time series manner, the signal includes the idle period with no output of the direct current waveform or pulse bursts between the direct current waveform period and the pulse bursts period.

The second current value of the direct current waveform is relatively low compared to the first current value of the pulse. In order to derive the relatively high first current value of the pulse from the relatively low second current value of the direct current waveform, the idle period with no output should be interposed therebetween. The controller may control the simulation module to generate a high energy pulse during this idle period.

In this connection, a length of the idle period will vary depending on a magnitude of the first current value of the pulse. The controller may control the nerve modulation device 10 such that the length of the idle period increases as the magnitude of the first current value of the pulse increases. That is, when the medical condition of the patient changes, the magnitude of the first current value of the pulse may change. Thus, the controller may control the nerve modulation device 10 to vary the length of the idle period.

In the nerve modulation device 10 in accordance with one embodiment of the inventive concept, burst stimulation based on the pulse bursts may adjust a magnitude of a nerve signaling in the nerve, and acts a signal for transmitting a signal toward a brain through an ascending tract to control a body state information processing scheme of the brain to induce symptom relief. That is, peripheral nerve stimulation through burst stimulation delivers electrical/chemical neurotransmission of peripheral nerves to the central nerve (brain), thereby treating central nervous system diseases. For example, when stimulating peripheral nerves, such as the trigeminal vagus nerve through the burst stimulus, the stimulus may be transmitted to the brain to regulate metabolism of a pain control region of the brain. This principle is regarded as a therapeutic principle of migraine.

In the neural modulation device 10 according to an embodiment of the inventive concept, direct current stimulation through a direct current waveform is used as a signal for increasing or decreasing spontaneous neural activity to induce the brain to recognize a certain physical condition. When sending the signal to the brain on the same principle as described above, or sending a signal only to internal organs or muscles where the nerve terminal extends, this leads the signal in a desired direction.

For example, applying electrical stimulation to the nerve based on the pulse bursts may suppress nerve signaling related to the patient's medical condition and thus may alleviate the patient's medical condition. Applying electrical stimulation to the nerve based on the direct current waveform may allow the patient to feel an induced state such as relaxation of the medical condition.

In some embodiments, the frequency of the pulse bursts may have a value between about 5 bursts per second and about 10 bursts per second. The duration of each pulse included in the pulse bursts period may have a value between about 45 µs and about 100 µs.

In some embodiments, a current magnitude of the pulse included in the pulse bursts period may have a value between approximately 10 mA and approximately 20 mA.

In some embodiments, a current magnitude of the direct current waveform may be about 0.1 mA to 1 mA, and may preferably have a value of approximately 0.5 mA.

Referring to FIG. 5, when the vagus nerve is the target nerve, the nerve modulation device 10 may be configured such that the first current value of the pulse included in the pulse bursts period is 20 mA, the frequency thereof is 10,000 Hz, the pulse duration thereof is 45 µs, the inter-pulse duration thereof is 5 to 10 µs (preferably 5 µs), the ramp up thereof is 60 to 900 s (preferably, 150 s), the ramp down thereof is 60 to 900 s (preferably 150 s), the total time thereof is 120 to 3,600 s (preferably 600 s), the burst frequency thereof is 10 Hz, and the burst duration thereof is at least 20 ms (preferably 20 ms), and the second current value of the direct current waveform is 0.5 mA.

In some embodiments, when the neck nerve is the target nerve, the nerve modulation device 10 may be configured such that the first current value of the pulse included in the pulse bursts period is 10 mA, the frequency thereof is 2,000 Hz, the pulse duration thereof is 100 µs, the inter-pulse duration thereof is 5 to 10 µs (preferably 5 µs), the ramp up thereof is 60 to 900 s (preferably, 150 s), the ramp down thereof is 60 to 900 s (preferably 150 s), the total time thereof is 120 to 3,600 s (preferably 600 s), the burst frequency thereof is 5 Hz, and the burst duration thereof is at least 70 ms (preferably 70 ms), and the second current value of the direct current waveform is 0.5 mA.

In some embodiments, when the trigeminal nerve is the target nerve, the nerve modulation device 10 may be configured such that the first current value of the pulse included in the pulse bursts period is 10 mA, the frequency thereof is 10,000 Hz, the pulse duration thereof is 45 µs, the inter-pulse duration thereof is 5 to 10 µs (preferably 5µs), the ramp up thereof is 60 to 900 s (preferably, 150 s), the ramp down thereof is 60 to 900 s (preferably 150 s), the total time thereof is 120 to 3,600 s (preferably 600 s), the burst frequency thereof is 10 Hz, and the burst duration thereof is at least 30 ms (preferably 30 ms), and the second current value of the direct current waveform is 0.5 mA.

The nerve modulation device 10 may be configured as shown in FIG. 5. In this connection, a result of applying electrical stimulation to the patient based on this configuration may be identified in FIGS. 6A and 6B, and FIGS. 7A and 7B.

First, referring to FIGS. 6A and 6B, an immediate stabilizing effect via parasympathetic nerve activation based on electrical stimulation in a stress situation compared to a baseline is identified with a HRV (Heart Rate Variability) main indicator.

Further, referring to FIGS. 7A and 7B, an immediate stabilizing effect via parasympathetic nerve activation based on electrical stimulation in a stress situation compared to a baseline is identified with an EDA (Electrical Dermal Activity) main indicator.

Figure 8:
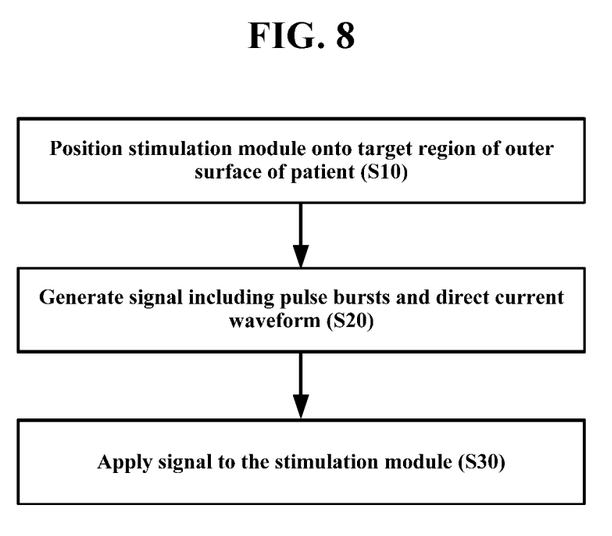
FIG. 8 is a flowchart of a method for treating a medical condition of a patient according to an embodiment of the inventive concept.

Hereinafter, referring to FIG. 8, a method for treating the medical condition of the patient or modulating the nerve of the patient using the nerve modulation device 10 according to embodiments of the inventive concept will be described. However, descriptions overlapping with the descriptions of the nerve modulation device 10 according to the above embodiments of the inventive concept will be omitted. FIG. 8 is a flow chart of a method for treating a medical condition of a patient according to one embodiment of the inventive concept.

Referring to FIG. 8, the method for treating the medical condition of the patient may include positioning the stimulation module 20 onto the target region of the patient's outer surface (S10), generating the signal including the pulse bursts and the direct current (DC) waveform (S20), and applying the signal to the stimulation module 20 such that electrical stimulation is applied to the nerve non-invasively through the outer face (S30).

In this connection, generating the signal (S20) includes generating the signal in which a current value of the direct current waveform in the direct current waveform period decreases from a relatively high first current value to a relatively low second current value, and in the direct current waveform period, a current value of the direct current waveform reaches the second current value and then is maintained to be substantially the second current value for a predetermined time. The information related to the generation of the signal as described above with reference to the nerve modulation device 10 according to the embodiments of the inventive concept may be equally applied to the method for treating the medical condition of the patient.

In one example, the frequency of the pulse bursts may have a value between about 5 bursts per second to about 10 burst per second. The duration of each pulse included in the pulse bursts period may range from approximately 45 µs to approximately 100 µs. The current value of the pulse included in the pulse bursts period may range from about 10 mA to about 20 mA. The current value of the direct current waveform may be approximately 0.5 mA. Details related to the characteristics of the pulse bursts and the direct current waveform have been described above in detail with reference to the nerve modulation device 10 according to the embodiments of the inventive concept.

The steps of the method or algorithm as described in connection with the embodiment of the inventive concept may be implemented directly in hardware, in a software module executed by hardware, or by a combination thereof. The software module may reside in RAM (Random Access Memory), ROM (Read Only Memory), EPROM (Erasable Programmable ROM), EEPROM (Electrically Erasable Programmable ROM), Flash Memory, Hard Disk, Removable Disk, CD-ROM, and any form of a computer readable recording medium well known in the art.

According to the inventive concept as described above, applying the signal including the pulse bursts and the direct current waveform to the patient non-invasively and thus applying electrical stimulation to the nerve of the patient may allow treating the medical condition of the patient, for example, allow relieving and relaxing symptoms of migraine, insomnia, neurologic disorder and depression.

The effects of the inventive concept are not limited to the effects mentioned above. Other effects as not mentioned will be clearly understood by those skilled in the art from the above descriptions.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A device for modulating a nerve of a patient by applying electrical stimulation to the nerve of the patient, the device comprising:
    a stimulation module comprising an electrode, and configured to apply a signal to the nerve of the patient; and
    a controller configured to control the signal to be applied by the stimulation module to the nerve of the patient,
    wherein the controller is further configured to:
    control the signal to include a direct current (DC) waveform period, a pulse bursts period and an idle period between the DC waveform period and the pulse bursts period, which are arranged alternately and are not overlapped,
    control the DC waveform period to include a DC waveform, and
    control the DC waveform not to be output in the idle period.

2. The device of claim 1, wherein the DC waveform having a first current value, and the controller is further configured to control the pulse bursts period to include a plurality of pulses, each of which has an output current value that is continuously changed from the first current value to a second current value.

3. The device of claim 2, wherein the controller is further configured to control the signal to include the DC waveform period, in which an application of the pulse bursts is deactivated.

4. The device of claim 2, wherein the controller is further configured to control the output current value of the DC waveform to be continuously decreased from the first current value to the second current value.

5. The device of claim 1, wherein the nerve includes at least one of a cranial nerve, a carotid sinus nerve, a vagus nerve, a cervical nerve, or a median nerve.

6. The device of claim 1, wherein the device is configured to apply the electrical stimulation to the nerve of the patient and thus to modulate the nerve to treat a medical condition of the patient.

7. The device of claim 6, wherein the stimulation module comprises a contact surface configured to be located on a target region of an outer surface of the patient, and
    wherein the signal for the electrical stimulation is applied to the nerve non-invasively through the outer surface.

8. The device of claim 7, wherein the target region includes at least one of forehead, ear, neck, or wrist.

9. The device of claim 6, wherein the medical condition of the patient includes at least one of migraine, insomnia, neurologic disorder, neuropathic pain, motor dysfunction, epilepsy, tinnitus, obesity, or depression.

10. The device of claim 1, wherein the controller is further configured to control at least one of a descent slope value of the DC waveform or a length of the idle period, based on a type of the medical condition of the patient to be treated.

11. The device of claim 10, wherein the controller is configured to set the first current value based on a type of the medical condition of the patient to be treated, and the controller is configured to increase a length of the idle period as a magnitude of the first current value increases.

12. The device of claim 1, wherein the controller is further configured to control the pulse bursts period to include the plurality of pulses with a frequency between approximately 5 bursts per second to approximately 10 bursts per second,
    wherein the controller is further configured to control the pulse bursts period to include the plurality of pulses, each of which has a duration between approximately 45 μs and approximately 100 μs.

13. The device of claim 12, wherein the controller is further configured to control the first current value to be between about 10 mA and about 20 mA, and control the second current value to be approximately 0.5 mA.

* * * * *